United States Patent
Farer et al.

(10) Patent No.: US 7,537,753 B2
(45) Date of Patent: May 26, 2009

(54) MOISTURE-PROOF MASCARA COMPOSITION

(75) Inventors: Alan Farer, Kinnelon, NJ (US); Yelena Loginova, Bronx, NY (US); Ralph Macchio, Sparta, NJ (US)

(73) Assignee: Coty B.V., Haarlem CC (NL)

( * ) Notice: Subject to any disclaimer, the term of this patent is extended or adjusted under 35 U.S.C. 154(b) by 436 days.

(21) Appl. No.: 10/520,561

(22) PCT Filed: Jul. 16, 2003

(86) PCT No.: PCT/EP03/07751

§ 371 (c)(1),
(2), (4) Date: Jan. 7, 2005

(87) PCT Pub. No.: WO2004/009043

PCT Pub. Date: Jan. 29, 2004

(65) Prior Publication Data

US 2005/0249687 A1 Nov. 10, 2005

(30) Foreign Application Priority Data

Jul. 18, 2002 (DE) .............................. 102 33 288

(51) Int. Cl.
*A61Q 1/10* (2006.01)
(52) U.S. Cl. ...................... 424/70.7; 424/70.6; 424/401
(58) Field of Classification Search ................ 424/70.7, 424/401
See application file for complete search history.

(56) References Cited

U.S. PATENT DOCUMENTS

| | | | |
|---|---|---|---|
| 5,534,247 | A | 7/1996 | Franjac |
| 5,599,547 | A | 2/1997 | Bartholomey |
| 5,800,825 | A * | 9/1998 | McMullen .................. 424/401 |
| 5,849,278 | A | 12/1998 | Piot |
| 5,874,072 | A | 2/1999 | Alwattari |
| 5,925,337 | A | 7/1999 | Arraudeau |
| 6,255,421 | B1 | 7/2001 | Plochocka |

| | | |
|---|---|---|
| 2004/0013624 | A1 | 1/2004 Mateu et al. |

FOREIGN PATENT DOCUMENTS

| | | |
|---|---|---|
| DE | 69101889 T2 | 12/1994 |
| DE | 100 33 527 A1 | 1/2002 |
| DE | 10033527 | 1/2002 |
| DE | 100 53 052 A1 | 6/2002 |
| EP | 0 557 196 A | 8/1993 |
| FR | 2 659 011 A | 9/1991 |
| WO | WO 99 20230 A | 4/1999 |
| WO | WO 9920230 A2 * | 4/1999 |
| WO | WO 02 30368 A | 4/2002 |

OTHER PUBLICATIONS

Hurschmann, B., "Hair Mascara", Apr. 29, 1999, WO 99/20230, English translation.*
Nowak et al., The Cosmetic Preparations vol. III, The Lipid and Emulsified Formulations, 4th ed., Publisher of Chemical Industry, Augsburg, 1994, p. 136.
Fiedler, Glossary of Excipients for Pharmaceutical, Cosmetics and Related Fields, Editio Cantor Publishing House, Aulendorf, 1996 pp. 342, 781, 1181.
Umbach, Cosmetics, Development, Manufacture and Application of Cosmetic Products, Georg Thieme Publishing, Stuttgart, 2nd 3d., 1995, pp. 317, 322 and 324.

* cited by examiner

*Primary Examiner*—Gina C Yu
(74) *Attorney, Agent, or Firm*—Novak Druce & Quigg; Gregory A. Nelson; Gregory M. Lefkowitz

(57) ABSTRACT

The invention relates to a moisture-resistant mascara composition with increased moisture and wear resistance. The mascara composition contains a complex, comprising 0.1 to 10 wt. % of a water-soluble polymer, selected from polyvinylpyrrolidone, vinyl acetate/vinyl pyrrolidone copolymers and mixtures thereof, 0.5 to 10 wt. % stearic acid and 1 to 40 wt. % of a wax or a wax mixture, whereby the complex exists as an oil phase emulsified in an aqueous phase and is produced by addition of the water-soluble polymer or copolymer to the oil phase, consisting of the molten wax or wax mixture and stearic acid, to form a stable colloidal complex and said complex is emulsified to give a homogeneous form with an aqueous phase. The complex, in which the water-soluble polymer is contained in the oil phase leads to mascaras with an exceptional plasticity and moisture resistance.

5 Claims, No Drawings

MOISTURE-PROOF MASCARA COMPOSITION

CROSS REFERENCE TO RELATED APPLICATION

This application is a national stage of PCT/EP2003/007751 filed 16 Jul. 2003 and based upon DE 102 33 288.6 filed 18 Jul. 2002 under the International Convention.

BACKGROUND OF THE INVENTION

1. Field of the Invention

The invention refers to a mascara composition with enhanced moisture-proofness and smear-proofness.

2. Related Art of the Invention

It is known to add polyvinylpyrrolidone into hairsprays or mascaras as a film-forming agent due to its good adhesion properties to keratinous substances. As a partly oil-soluble, but above all water-soluble material, polyvinylpyrrolidone has hygroscopic properties which reduce the stability of the end product once it has been applied on to the hair or eyelashes and contribute to the mascara being smeared thus reducing the time it lasts.

U.S. Pat. No. 6,255,421 describes a polymerization process for manufacturing a vinyl polymer from vinyl monomers, such as e.g. vinyl pyrrolidone or comonomers of vinyl pyrrolidone with vinyl acetate, in which process a polymer powder soaked in oil can be produced which subsequently can be combined with water and processed into a homogeneous liquid emulsion. This requires special processing steps.

SUMMARY OF THE INVENTION

The object of the invention is to provide a mascara composition with enhanced moisture-proofness and smear-proofness and which has excellent adhesion properties.

According to the invention, the mascara composition is characterized by a complex consisting of 0.1 to 10% by weight of a water-soluble polymer selected from among polyvinylpyrrolidone, vinyl acetate/vinyl pyrro-lidone copolymers and mixtures thereof, 0.5 to 10% by weight of stearic acid and 1 to 40% by weight of a wax or wax mixture, the said complex being present in the form of an oil phase emulsified in an aqueous phase.

In the mascara according to the invention, the water-soluble polymer is not dissolved in the aqueous phase as in previously known preparations, but is part of the oil phase and, jointly with waxes and Stearic Acid, forms a complex which has unusual physical properties. The said complex has a very good plasticity compared to the wax mixture or wax which are commonly used. Compared to the simple polymer film on the surface of the hair/eyelashes, the complex has a considerably enhanced moisture-proofness and adheres to the eyelashes very well.

Since mascara compositions are semi-liquid (or semi-solid) substances, the product's characteristics as regards spreading and solidification are essential features each time the mascara is used. The present invention provides a product where there is enough time to spread the mascara on the eyelashes and which ensures that the aim, i.e. thicker, longer and more clearly defined eyelashes, is achieved with no undesired negative effects occurring. This is made possible by including the water-soluble polymer into the oil phase thus creating improved possibilities for composing the product in a way that e.g. it makes the eyelashes seem thicker. The essential feature of the product according to the invention consists in that smear-proofness is enhanced and the hygroscopic properties of the water-soluble polymer minimized.

It was further found that through the combination of PVP or the VA/VP copolymer (in the following: PVP) with the wax and the stearic acid and the application of strong mechanical forces at temperatures in the melting range of the waxes, or 70-75° C., a very homogeneous and stable complex is generated, which is not a complex based on chemical bonds, but represents a very stable colloidal system, from which PVP even upon a later contact with the aqueous phase falls out not at all or only in a very limited manner. This means the inter-molecular forces are so strong to essentially prevent a drifting of the PVP.

Experiments with 4%/wt PVP in wax or in water have shown that after evaporation of the whole water 5%/wt of solids were obtained with PVP/wax, which by the increase of 1%/wt already indicates that a structural change has occurred, while with PVP/water the input 4%/wt solids were obtained. It was further found that with the complex in accordance with the invention large shiny, slightly yellow, harder crystals were microscopically recognizable as residue, while in the other case of PVP solubilized in water only very small particles were formed.

Further auxiliaries, carrier substances and active agents or mixtures thereof can be added to the aqueous phase or oil phase or as a separate phase, depending upon their solubility and miscibility.

A preferred share of stearic acid is in the range of 2 to 8% by weight. A preferred share of wax which is preferably a mixture of some waxes is in the range of 10 to 28% by weight.

The ratio of water soluble polymer or copolymer to stearic acid can be for the polymer 0.1 to 50% by weight and for stearic acid 50 to 99.1% by weight.

The mascara composition according to the invention contains further auxiliaries, carrier substances, active agents or mixtures thereof.

Included are preservatives, colorings, pigments with coloring effect, thickeners, fragrances, alcohols, polyols, electrolytes, gelling substances, polar and nonpolar oils, further polymers and/or copolymers, emulsifiers, waxes, stabilizers.

In a preferred embodiment, the complex does not contain any esters which are able to dissolve the polymer or copolymer.

Pigments, pigment mixtures or powders with a pigment-like effect, also including those with a pearl-gloss effect, may include, for example, iron oxides, aluminum silicates such as ochre, titanium (di)oxide, mica, kaolin, manganese containing clays such as umber and red bole, calcium carbonate, French chalk, mica-titanium oxide, mica-titanium oxide-iron oxide, bismuth oxychloride, nylon beads, ceramic beads, expanded and non-expanded synthetic polymer powders, cellulose/rayon, teflon, cotton fibers, powdery natural organic compounds such as milled solid algae, milled plant parts, encapsulated and non-encapsulated cereal starches and mica-titanium oxide-organic dye.

Antioxidants include vitamins such as vitamin C and derivatives thereof, for example, ascorbic acetate, ascorbic phosphate, and ascorbic palmitate; vitamin A and derivatives thereof; folic acid and derivatives thereof; vitamin E and derivatives thereof, such as tocopheryl acetate; flavones or flavonoids; amino acids, such as histidine, glycine, tyrosine, tryptophan, and derivatives thereof; carotenoids and carotenes such as, for example, α-carotene, β-carotene; uric acid and derivatives thereof; α-hydroxy acids such as citric acid, lactic acid, malic acid; stilbene and derivatives thereof etc.

Mascaras with the composition according to the invention may exist as O/W or W/O emulsions. Suitable emulsifiers for O/W emulsions are for instance addition products of 2-30 mol ethylene oxide to linear $C_8$-$C_{22}$ fatty alcohols, to $C_{12}$-$C_{22}$ fatty acids and to $C_8$-$C_{15}$ alkylphenols; $C_{12}$-$C_{22}$ fatty acid monoesters and diesters of addition products of 1-30 mol ethylene oxide to glycerine. Preferred emulsifiers are e.g. Polysorbate 20.

For W/O emulisons it is preferred to incorporate the emulsifier at a different step after the above mentioned complex is formed. Copolymers of polysiloxan polyalkyl polyethers are possible emulsifiers. A preferred emulsifier is Cetyl Dimethicone Copolyol.

It is moreover advantageous to add to the compositions according to the invention corresponding water and/or oil soluble UVA or UVB filters or both. Advantageous oil-soluble UVB filters include 4-amino benzoic acid derivatives such as 4-(dimethylamino)-benzoic acid-(2-ethylhexyl) ester; esters of cinnamic acid such as 4-methoxy cinnamic acid (2-ethylhexyl) ester, benzophenone derivatives such as 2-hydroxy-4-methoxy benzophenone; 3-benzylidene camphor derivatives such as 3-benzylidene camphor.

Preferred oil-soluble UV filters are Benzophenone-3, Butyl-Methoxybenzoylmethane, Octyl Methoxycinnamate, Octyl Salicylate, 4-Methylbenzylidene Camphor, Homosalate and Octyl Dimethyl PABA.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters include dibenzoyl methane derivatives such as 1-phenyl-4-(4'-isopropanol phenyl) propane-1,3-dione.

Further additives are, for example, selected among castor oil, paraffin oil, myristyl lactate, isopropyl myristate, isopropyl lanolate, isopropyl palmitate, p-hydroxybenzoic acid propyl ester.

The waxes may be selected among natural plant wax, animal wax, natural and synthetic mineral wax and synthetic wax. This includes for example carnauba wax, candelilla wax, ozokerite, beeswax, montan wax, wool wax, ceresine, micro-waxes, paraffin waxes, petrolatum, silicone, polyethylenglycol(ester) waxes, microcrystalline wax. Mixtures of some waxes are preferred, such as paraffin wax, carnauba wax and beeswax.

Comparative tests were carried through e.g. a humidity test versus commercial PVP/VA Copolymer (Luviskol®VA64W) using a humidity chamber at 32° C., 80% of humidity for 24 hr.

The wax complex of: Beeswax/Stearic Acid/Carnauba wax/Candelilla and PVP at a ratio of 6:5:2:1:4 and commercially available PVP/VA Copolymer have been applied on inert substrate in 200 micron film until completely dry. Then specimens have been placed into humidity chamber for 24 hr.

The weight of specimens has been recorded in following order:
Weight of the substrate
Weight of the wet film
Weight of the dry film before the humidity chamber
Weight of the film after the humidity chamber The results showed that wax/stearic acid/PVP complex exhibits in 2 times better moisture-resistance compared to commercial PVP/VA Copolymer. This shows clearly the considerably enhanced moisture-proofness.

The invention further concerns a method for manufacturing a moisture-proof mascara composition which comprises that an oil phase consisting of waxes or wax mixtures and Stearic Acid is heated until it melts, a particulate water-soluble polymer selected from among Polyvinylpyrrolidone, vinyl acetate/vinyl pyrrolidone copolymers and mixtures thereof is added into the melted mass while stirring at a rate of 100 to 2500 rpm until a homogeneous mixture is obtained, and, a) if a W/O emulsion is to be produced, pigments are added into the homogeneous mixture of the oil phase until they are completely dispersed, and an aqueous phase consisting of water and optionally further auxiliaries, carrier substances, active agents and mixtures thereof is added, the mixture is stirred at temperatures ranging from 60 to 75° C. until a homogeneous emulsion is obtained and the homogeneous mixture is cooled, or b) if an O/W emulsion is to beproduced, after addition of the pigments into the aqueous phase consisting of water and optionally further auxiliaries, carrier substances, active agents and mixtures thereof, and until they are dispersed, the above mentioned oil phase is added into the aqueous phase and the mixture is stirred at temperatures ranging from 60 to 75° C. until a homogeneous emulsion is obtained and subsequently cooled.

The product obtained no longer exhibits two phases, but is a homogeneous substance in which thermodynamic factors and surface-active compounds (stearic acid) maintain all particles together.

In the following, the invention shall be described in detail by examples. All percent figures are by weight if not other set out.

EXAMPLE 1

Mascara I

| Phase A | |
|---|---|
| Paraffin wax | 6 |
| Carnauba wax | 4 |
| Beeswax | 3.5 |
| Stearic Acid | 5.5 |
| Synthetic wax | 3 |
| Cetyl Dimethicone Copolyol | 1 |
| Phase B | |
| Polyvinylpyrrolidone | 4 |
| Phase C | |
| Water | ad 100 |
| Polyvinyl Alcohol | 3 |
| Phase D | |
| Pigments | 8 |
| Phase E | |
| Triethanolamine | 2.2 |
| Phase F | |
| Preservative | 0.2 |

Phase A was heated up to 80° C. until stirring. Phase B was sprinkled under homogenization at about 1100 rpm to phase A. The mixture was homogenized for 20 min with about 1500 rpm.

Phase D was added and the mixture homogenized until full dispersion of the pigments. After that phase C and E were added and emulsified at 65° C. Finally phase F was added at about 40° C.

The mixture was cooled down to 30° C. and transferred to suitable storage containers.

EXAMPLE 2

Mascara II

| Phase A | |
|---|---|
| Water | q.s. to 100% |
| Preservative | 0.3 |
| Polyquarternium-10 | 0.3 |
| Triethanolamine, 99% | 1.5 |
| Polysorbate 20 | 1.0 |
| Propylene Glycol | 4.0 |
| Phase B | |
| Pigments | 10 |
| Phase C | |
| Synthetic Beeswax | 4.0 |
| Carnauba wax | 3.0 |
| Microcrystalline wax | 5.0 |
| Stearic Acid | 6.0 |
| Hydrogenated Castor oil | 2.0 |
| Phase D | |
| PVP | 3.0 |

Procedure:

Water was heated up to 70-75° C. The rest of the ingredients were added in sequence order. Phase B was added thereafter and homogenized until fully dispersed. Phase C was melted until clear. The temperature was maintained at 75-80° C. Phase D was added to the phase C with moderate mixing until homogeneous. Oil was added to the water and emulsified.

The batch was cooled down to 30° C. and transferred to suitable storage containers.

We claim:

1. A moisture-proof mascara composition, characterized by a stable colloidal complex comprising
    0.1 to 10% by weight of a water-soluble polymer selected from among polyvinyl-pyrrolidone, vinyl acetate/vinyl pyrrolidone copolymers and mixtures thereof,
    0.5 to 10% by weight of stearic acid and
    1 to 40% by weight of a wax or wax mixture,
    and manufactured by adding the water-soluble polymer or copolymer into the oil phase consisting of the melted wax or wax mixture, stearic acid and optionally an emulsifier, until a stable colloidal complex is formed, and emulsifying the said complex in homogeneous form with an aqueous phase.

2. The mascara composition according to claim 1, wherein the complex does contain further auxiliaries, carrier substances, active agents or mixtures thereof.

3. The mascara composition according to claim 1, wherein the composition comprises an emulsifier for the oil phase and the aqueous phase.

4. The mascara composition according to claim 1, comprising 10 to 28% by weight of a wax or wax mixture.

5. A method for manufacturing the moisture-proof mascara composition of claim 1 wherein an oil phase consisting of waxes or wax mixtures and Stearic Acid is heated until it melts, a particulate water-soluble polymer selected from among polyvinylpyrrolidone, vinyl acetate/vinyl pyrrolidone copolymers and mixtures thereof is added into the melted mass while stirring at a rate of 100 to 2500 rpm until a homogeneous mixture is obtained, and,
    a) if a W/O emulsion is to be produced, pigments are added into the homogeneous mixture until they are completely dispersed, and an aqueous phase consisting of water and optionally further auxiliaries, carrier substances, active agents and mixtures thereof is added, the mixture is stirred at temperatures ranging from 60 to 75° C. until a homogeneous emulsion is obtained and the homogeneous mixture is cooled, or
    b) if an O/W emulsion is to be produced, after addition of the pigments into the aqueous phase and alter their dispersion, the oil phase is added into the aqueous phase and the mixture is stirred at temperatures ranging from 60 to 75° C. until a homogeneous emulsion is obtained and subsequently cooled.

* * * * *